US00PP20406P2

(12) United States Plant Patent
Barends

(10) Patent No.: US PP20,406 P2
(45) Date of Patent: Oct. 13, 2009

(54) *GERANIUM* PLANT NAMED 'FIDANOL RED'

(50) Latin Name: *Pelargonium peltatum*
Varietal Denomination: Fidanol Red

(75) Inventor: Eveline Barends, De Lier (NL)

(73) Assignee: Fides B.V., De Lier (NL)

( * ) Notice: Subject to any disclaimer, the term of this patent is extended or adjusted under 35 U.S.C. 154(b) by 78 days.

(21) Appl. No.: 12/154,248

(22) Filed: May 21, 2008

(51) Int. Cl.
*A01H 5/00* (2006.01)

(52) U.S. Cl. ..... Plt./332

(58) Field of Classification Search ..... Plt./332
See application file for complete search history.

*Primary Examiner*—Kent L. Bell
(74) *Attorney, Agent, or Firm*—C. A. Whealy

(57) ABSTRACT

A new and distinct cultivar of Ivy *Geranium* plant named 'Fidanol Red', characterized by its upright and slightly outwardly spreading growth habit; mounding and rounded plant habit; freely branching habit; dark green-colored leaves; freely flowering habit; dark red-colored flowers; and good garden performance.

1 Drawing Sheet

Botanical designation: *Pelargonium peltatum.*
Cultivar denomination: 'Fidanol Red'.

BACKGROUND OF THE INVENTION

The present invention relates to a new and distinct cultivar of Ivy *Geranium*, botanically known as *Pelargonium peltatum,* and hereinafter referred to by the name 'Fidanol Red'.

The new Ivy *Geranium* is a product of a planned breeding program conducted by the Inventor in De Lier, The Netherlands. The objective of the breeding program is to create new freely-branching and freely-flowering Ivy *Geranium* cultivars that flower early and have attractive foliage and flower coloration.

The new Ivy *Geranium* originated from a cross-pollination made by the Inventor in De Lier, The Netherlands of two unnamed proprietary selections of *Pelargonium peltatum,* not patented. The cultivar Fidanol Red was discovered and selected by the Inventor as a flowering plant from within the progeny of the stated cross-pollination in a controlled greenhouse environment in De Lier, The Netherlands, in 2005.

Asexual reproduction of the new Ivy *Geranium* by vegetative terminal cuttings in a controlled greenhouse environment in De Lier, The Netherlands, since 2005, has shown that the unique features of this new Ivy *Geranium* are stable and reproduced true to type in successive generations.

SUMMARY OF THE INVENTION

The cultivar Fidanol Red has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Fidanol Red'. These characteristics in combination distinguish 'Fidanol Red' as a new and distinct cultivar of Ivy *Geranium*:

1. Upright and slightly outwardly spreading growth habit; mounding and rounded plant habit.
2. Freely branching habit.
3. Dark green-colored leaves.
4. Freely flowering habit.
5. Dark red-colored flowers.
6. Good garden performance.

Plants of the new Ivy *Geranium* differ primarily from plants of the parent selections in plant size and uniformity as plants of the new *Geranium* are more compact and more uniform than plants of the parent selections.

Plants of the new Ivy *Geranium* can be compared to plants of *Pelargonium peltatum* 'Meririco', disclosed in U.S. Plant Pat. No. 10,245. In side-by-side comparisons conducted in De Lier, The Netherlands, plants of the new Ivy *Geranium* differed from plants of 'Meririco' primarily in flower color as plants of the new Ivy *Geranium* have darker red-colored flowers than plants of 'Meririco'. In addition, plants of the new Ivy *Geranium* were more compact than plants of 'Meririco'.

BRIEF DESCRIPTION OF THE PHOTOGRAPH

The accompanying colored photograph illustrates the overall appearance of the new Ivy *Geranium*, showing the colors as true as it is reasonably possible to obtain in colored reproductions of this type. Colors in the photograph may differ slightly from the color values cited in the detailed botanical description which accurately describe the colors of the new Ivy *Geranium*. The photograph comprises a side perspective view of a typical flowering plant of 'Fidanol Red' grown in a container.

DETAILED BOTANICAL DESCRIPTION

The aforementioned photograph and following observations, measurements and values describe plants grown in De Lier, The Netherlands in a glass-covered greenhouse during the autumn and winter and under conditions which closely approximate commercial production. During the production of the plants, day temperatures ranged from 14° C. to 16° C. and night temperatures ranged from 12° C. to 14° C. Plants were eight weeks old when the photograph and the description were taken. In the detailed description, color references are made to The Royal Horticultural Society Colour Chart, 1995 Edition, except where general terms of ordinary dictionary significance are used.

Botanical classification: *Pelargonium peltatum* 'Fidanol Red'.

Parentage:

*Female, or seed, parent.*—Unnamed proprietary selection of *Pelargonium peltatum,* not patented.

*Male or pollen parent.*—Unnamed proprietary selection of *Pelargonium peltatum,* not patented.

Propagation:

*Type.*—By vegetative terminal cuttings.

*Time to initiate roots, summer.*—About four days at temperatures of 22° C.

*Time to initiate roots, winter.*—About six days at temperatures of 22° C.

*Time to produce a rooted young plant, summer.*—About 14 days at temperatures of 22° C. to 30° C.

*Time to produce a rooted young plant, winter.*—About 16 days at temperatures of 20° C. to 25° C.

*Root description.*—Medium in thickness, fibrous; whitish grey in color.

*Rooting habit.*—Freely branching, moderately dense.

Plant description:

*General appearance.*—Upright and outwardly spreading growth habit; rounded and uniformly mounded plant habit; with development, trailing; densely foliated.

*Growth and branching habit.*—Moderately vigorous to vigorous growth habit. Freely basal branching habit with about ten lateral branches developing per plant.

*Plant height, to top of umbels.*—About 20 cm to 25 cm.

*Plant width.*—About 12 cm to 20 cm.

*Lateral branches.*—Length: About 5 cm to 18 cm. Diameter: About 3 mm to 6 mm. Internode length: About 3 cm to 6 cm. Texture: Pubescent. Strength: Moderately strong. Color: Close to 144C.

Foliage description:

*Arrangement.*—Alternate; simple.

*Length.*—About 5 cm to 8 cm.

*Width.*—About 5 cm to 10 cm.

*Shape.*—Orbicular.

*Apex.*—Acute.

*Base.*—Cordate.

*Margin.*—Crenate; slightly undulate.

*Venation pattern.*—Palmate.

*Texture, upper surface.*—Smooth, glabrous.

*Texture, lower surface.*—Slightly pubescent.

*Color.*—Developing foliage, upper surface: Close to 143A. Developing foliage, lower surface: Close to 143C. Fully developed, upper surface: Close to 137A; venation, close to 143D. Fully developed, lower surface: Between 137C and 138A; venation, close to 143D. Zonation pattern: Faint, close to 177A in color.

*Petiole.*—Length: About 3.5 cm to 7 cm. Diameter: About 3 mm. Texture, upper and lower surfaces: Pubescent. Color, upper and lower surfaces: Close to 143C.

Flower description:

*Flower arrangement.*—Semi-double rotate flowers arranged in rounded hemispherical umbels arising from apical leaf axils. Umbels displayed above the foliage on strong peduncles. Flowers face upright to outward. Flowers not fragrant.

*Quantity of flowers.*—Freely flowering habit; about ten umbels develop per plant, each umbel each with about 10 to 30 flowers.

*Flowering season.*—Year-round under greenhouse conditions. In an outdoor nursery in De Lier, The Netherlands, flowering is continuous from late spring until frost in the autumn.

*Flower longevity.*—Individual flowers last about two to 14 days on the plant. Flowers persistent.

*Umbel height.*—About 4 cm to 7 cm.

*Umbel diameter.*—About 4 cm to 9 cm.

*Flower diameter.*—About 4 cm.

*Flower depth* (*height*).—About 2 cm.

*Flower buds.*—Length: About 6 mm to 8 mm. Diameter: About 3 mm to 6 mm. Shape: Broadly elliptical. Color: Close to 143C.

*Petals.*—Quantity per flower: About five to 20. Length: About 2 cm to 3.5 cm. Width: About 5 mm to 10 mm. Shape: Lanceolate to ovate. Apex: Acute. Base: Attenuate. Margin: Entire. Texture, upper and lower surfaces: Smooth, glabrous; velvety. Color: When opening, upper surface: Close to 46A. When opening, lower surface: Close to 45A. Fully opened, upper and lower surfaces: Close to 45A; color becoming closer to 53A with development.

*Petaloids.*—Quantity per flower: Typically one to 15. Length: About 1 mm to 2 cm. Width: About 1 mm to 9 mm. Shape: Irregularly shaped; narrowly obovate to irregularly oblanceolate. Apex: Rounded. Base: Attenuate. Margin: Entire. Texture, upper and lower surfaces: Smooth, glabrous. Color: When opening, upper and lower surfaces: Close to 46A. Fully opened, upper and lower surfaces: Close to 45A.

*Sepals.*—Quantity per flower: Five, arranged in a single whorl. Length: About 1 cm. Width: About 3 mm to 4 mm. Shape: Lanceolate. Apex: Acute. Base: Cuneate. Margin: Entire. Texture, upper and lower surfaces: Densely pubescent. Color, immature, upper and lower surfaces: Close to 144A. Color, mature, upper and lower surfaces: Close to 144A.

*Peduncle* (*umbel stem*).—Length: About 8 cm to 15 cm. Diameter: About 3 mm to 4 mm. Strength: Moderately strong. Angle: Erect to about 30° C. from vertical. Texture: Pubescent. Color: Close to 144A.

*Pedicel* (*individual flower stem*).—Length: About 2 cm to 3 cm. Diameter: About 3 mm to 15 mm. Strength: Moderately strong. Angle: Erect to about 90° C. from vertical. Texture: Pubescent. Color: Close to 144A.

*Reproductive organs.*—Androecium: Stamen quantity per flower: About one to eight. Filament length: About 7 mm. Filament color: Close to 155A. Anther length: About 2 mm. Anther shape: Oblong. Anther color: Close to 183A to 183B. Pollen amount: Moderate. Pollen color: Close to 172C. Gynoecium: Pistil quantity per flower: About ten to 15. Pistil length: About 3 mm. Stigma shape: Tapering; reflexed. Stigma color: Close to 50C. Style length: About 3 mm. Style color: Close to 27B. Ovary color: Close to 141C.

*Seed.*—Seed development has not been observed.

Disease/pest resistance: Plants of the new Ivy *Geranium* have not been observed to be resistant to pathogens and pests common to Ivy *Geraniums*.

Garden performance: Plants of the new Ivy *Geranium* have been observed to tolerate rain, wind, and temperatures ranging from about 0° C. to about 45° C. and have demonstrated good garden performance.

It is claimed:

1. A new and distinct Ivy *Geranium* plant named 'Fidanol Red' as illustrated and described.

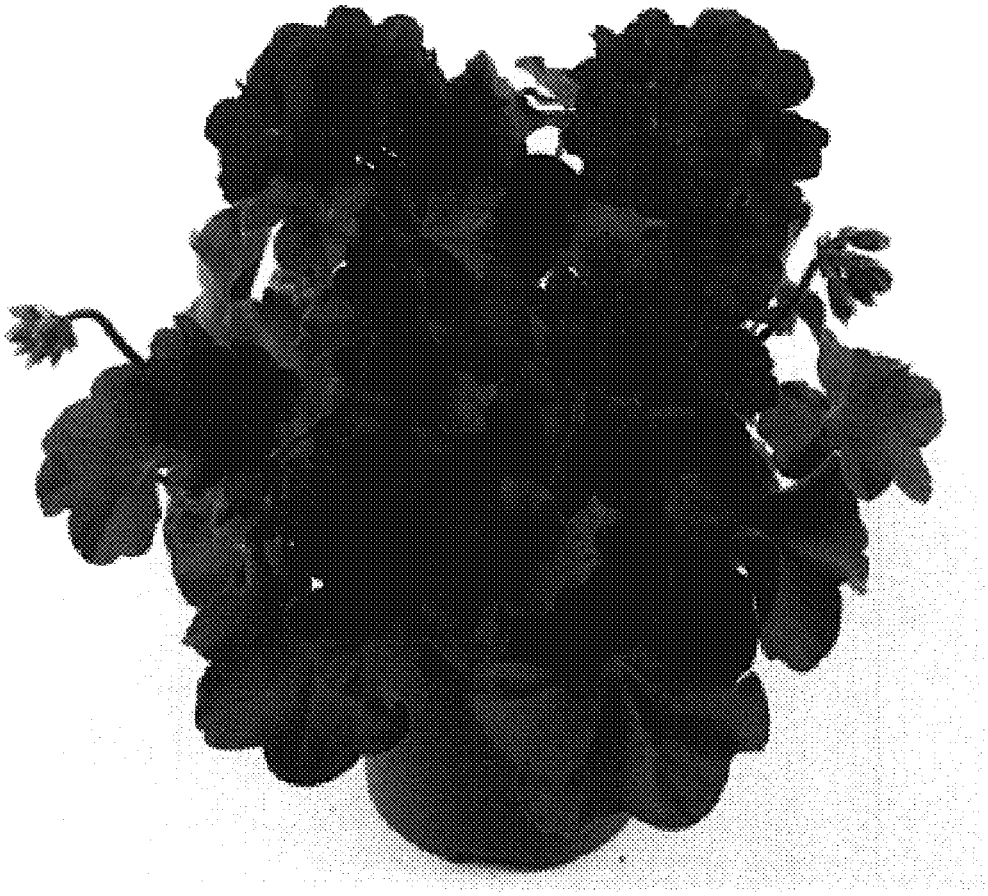

* * * * *